(12) United States Patent
Cordaro et al.

(10) Patent No.: US 8,097,036 B2
(45) Date of Patent: *Jan. 17, 2012

(54) MOTION RESTORING INTERVERTEBRAL DEVICE

(75) Inventors: Nicholas M. Cordaro, Vista, CA (US); Colin M. Smith, Dana Point, CA (US)

(73) Assignee: SeaSpine, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/919,616

(22) PCT Filed: Apr. 28, 2006

(86) PCT No.: PCT/US2006/016399
§ 371 (c)(1),
(2), (4) Date: Oct. 30, 2007

(87) PCT Pub. No.: WO2006/119092
PCT Pub. Date: Nov. 9, 2006

(65) Prior Publication Data
US 2009/0054986 A1    Feb. 26, 2009

Related U.S. Application Data

(60) Provisional application No. 60/676,744, filed on May 2, 2005.

(51) Int. Cl.
*A61F 2/44* (2006.01)
(52) U.S. Cl. .................................................. 623/17.15
(58) Field of Classification Search .... 623/17.11–17.16, 623/23.7, 23.71, 23.72, 23.73, 23.74, 23.75, 623/23.76, 23.28, 23.29, 23.3, 23.53, 23.54, 623/23.55, 23.6, 23.61
See application file for complete search history.

(56) References Cited

U.S. PATENT DOCUMENTS

| | | | | |
|---|---|---|---|---|
| 5,425,773 A | * | 6/1995 | Boyd et al. | 623/17.15 |
| 5,676,701 A | * | 10/1997 | Yuan et al. | 623/17.15 |
| 5,755,796 A | | 5/1998 | Ibo et al. | |
| 5,899,941 A | * | 5/1999 | Nishijima et al. | 623/17.15 |
| 6,113,637 A | * | 9/2000 | Gill et al. | 623/17.15 |
| 6,113,638 A | | 9/2000 | Williams et al. | |
| 6,206,924 B1 | | 3/2001 | Timm | |
| 6,368,350 B1 | | 4/2002 | Erickson et al. | |
| 6,517,580 B1 | | 2/2003 | Ramadan et al. | |
| 6,572,619 B2 | | 6/2003 | Santilli | |

(Continued)

FOREIGN PATENT DOCUMENTS

DE    2263842    12/1972

(Continued)

OTHER PUBLICATIONS

Hoffmann-Daimler, Intervertebral Disk Displacement, vol. 112, No. 4, Aug. 1974.

(Continued)

*Primary Examiner* — Alvin J. Stewart

(57) ABSTRACT

A motion restoring intervertebral device includes first and second articulating components positioned between adjacent vertebrae with the articulating surface of the first component being formed by a circular domed convex projection having a first radius. The articulating surface of the second component is formed by a generally concave recess having the first radius in the medial-lateral direction and a second larger sweeping radius in the interior-posterior direction so that the components are capable of rotating against each other in all directions and translate against each other in the anterior-posterior direction, whereby translation away from the center of the first radius will produce device and joint distraction to limit excessive translation.

12 Claims, 6 Drawing Sheets

U.S. PATENT DOCUMENTS

| | | | |
|---|---|---|---|
| 6,595,998 B2 | 7/2003 | Johnson et al. | |
| 6,673,075 B2 | 1/2004 | Santilli | |
| 6,699,288 B2 | 3/2004 | Moret | |
| 6,706,068 B2 | 3/2004 | Ferree | |
| 6,736,849 B2 | 5/2004 | Li et al. | |
| 6,743,257 B2 | 6/2004 | Castro | |
| 6,758,862 B2 | 7/2004 | Berry et al. | |
| 6,793,678 B2 | 9/2004 | Hawkins | |
| 6,800,092 B1 | 10/2004 | Williams et al. | |
| 6,802,863 B2 * | 10/2004 | Lawson et al. | 623/17.16 |
| 6,805,714 B2 | 10/2004 | Sutcliffe | |
| 6,899,735 B2 | 5/2005 | Coates et al. | |
| 6,966,929 B2 | 11/2005 | Mitchell | |
| 7,048,764 B2 * | 5/2006 | Ferree | 623/17.15 |
| 7,156,876 B2 | 1/2007 | Moumene et al. | |
| 7,198,643 B2 * | 4/2007 | Zubok et al. | 623/17.15 |
| 7,217,293 B2 | 5/2007 | Branch, Jr. | |
| 7,235,101 B2 | 6/2007 | Berry et al. | |
| 7,250,060 B2 | 7/2007 | Trieu | |
| 7,276,082 B2 * | 10/2007 | Zdeblick et al. | 623/17.15 |
| 7,331,994 B2 * | 2/2008 | Gordon et al. | 623/17.13 |
| RE40,260 E * | 4/2008 | Buhler | 623/17.15 |
| 7,494,507 B2 * | 2/2009 | Dixon et al. | 623/17.14 |
| 7,494,508 B2 * | 2/2009 | Zeegers | 623/17.15 |
| 7,517,363 B2 | 4/2009 | Rogers et al. | |
| 7,537,612 B2 | 5/2009 | Kunzler | |
| 7,563,284 B2 | 7/2009 | Coppes et al. | |
| 2003/0045939 A1 | 3/2003 | Casutt | |
| 2003/0199981 A1 | 10/2003 | Ferree | |
| 2004/0082999 A1 * | 4/2004 | Mathys et al. | 623/17.11 |
| 2004/0243241 A1 * | 12/2004 | Istephanous et al. | 623/17.14 |
| 2005/0033438 A1 | 2/2005 | Schultz et al. | |
| 2005/0038516 A1 | 2/2005 | Spoonamore | |
| 2005/0043803 A1 | 2/2005 | Schultz et al. | |
| 2005/0055098 A1 * | 3/2005 | Zdeblick et al. | 623/17.11 |
| 2005/0154462 A1 * | 7/2005 | Zucherman et al. | 623/17.15 |
| 2005/0159818 A1 * | 7/2005 | Blain | 623/17.15 |
| 2005/0197706 A1 * | 9/2005 | Hovorka et al. | 623/17.15 |
| 2005/0283242 A1 * | 12/2005 | Zucherman et al. | 623/17.15 |
| 2006/0116769 A1 * | 6/2006 | Marnay et al. | 623/17.15 |
| 2006/0136061 A1 * | 6/2006 | Navarro et al. | 623/17.13 |
| 2009/0082868 A1 | 3/2009 | Cordaro et al. | |
| 2009/0210060 A1 * | 8/2009 | de Villiers et al. | 623/17.14 |

FOREIGN PATENT DOCUMENTS

| | | |
|---|---|---|
| WO | 2004/064692 | 8/2004 |
| WO | 2005/025431 | 3/2005 |

OTHER PUBLICATIONS

Trouillier, H. et al., "Report on Two Failed Posterior Lumbar Interbody Fusions", SICOT Online Report E034: Accepted May 6, 2003, Department of Orthopedic Surgery, Institute of Pathology, Ludwig-Maximilians University, Munich, Germany, pp. 1-12.

Salmang, H. et al. "Keramik Teil 1", 1982, Springer, DE, Berlin (UA.) Germany, XP002641702, p. 236.

Williams, D.F. "The Williams Dictionary of Biomaterials", Jan. 1, 1999, Liverpool University Press, GB, Liverpool, GB, p. 139 (XP-002641703).

EP Application No. 06769925 Supplementary Search Report dated Jun. 14, 2011, 12 pages.

EP Application No. 06751878 Supplementary Search Report dated Jun. 16, 2011, 6 pages.

* cited by examiner

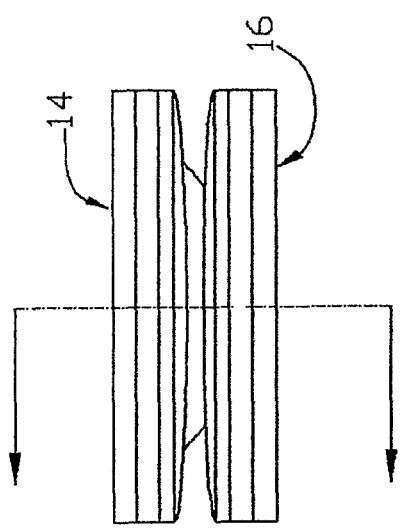
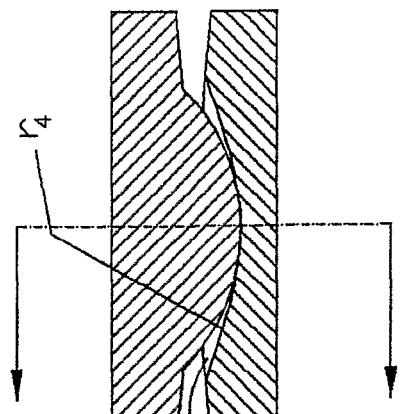
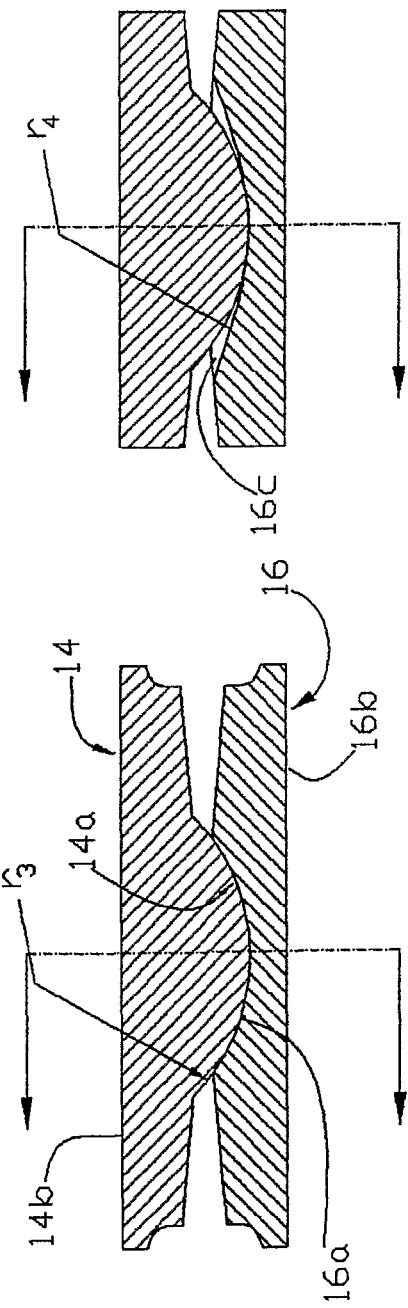
Figure 4A
Figure 4B
Figure 4C

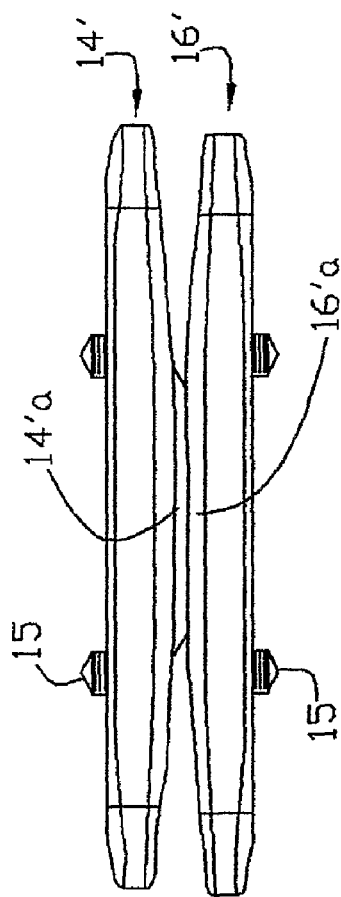
Figure 5
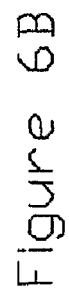
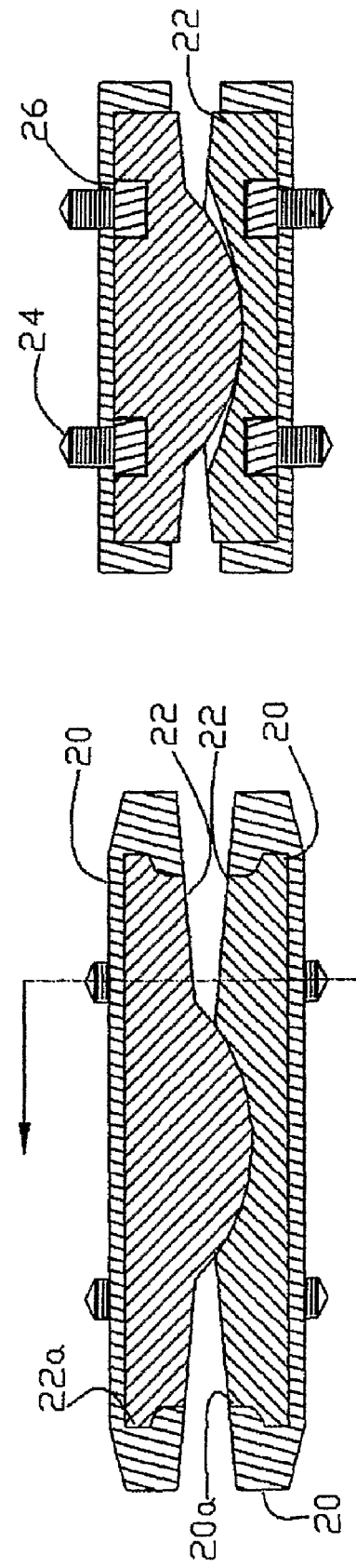
Figure 6A
Figure 6B

MOTION RESTORING INTERVERTEBRAL DEVICE

RELATED APPLICATION

This application is based on and claims priority of U.S. Provisional Application No. 60/676,744 ("'744 application") for a Motion Restoring Intervertebral Device filed on May 2, 2005, the contents of the provisional application are incorporated herein by reference.

FIELD OF THE INVENTION

This application relates to intervertebral devices to partially or completely replace a natural spinal disc.

BACKGROUND OF THE INVENTION

Endeavors to treat low back pain by means of a motion restoring intervertebral element have existed for many decades. Hoffmann-Daimler disclosed many such inventions in the Germany patent 2,263,842. These included ball and socket prostheses with single and/or dual articulations and with and without motion dampening elements. The clinical use of the device containing a ball supported by two opposing sockets extending from generally flat plates, was discussed in Hoffmann-Daimler's 1974 article published in Intervertebral Disk Displacement, Vol. 112, No. 4, August 1974. Hansen et al., U.S. Pat. No. 5,676,701, disclosed a low wear artificial spinal disc having opposing convex and concave contoured surfaces with a full 360 degree circumference. This allows for rotation but no translation. Yuichiro and Koichi, U.S. Pat. No. 5,899,941, disclosed a similar device but where the articulating surface is generally non-conforming to allow rotation and translational movement. This is similar to U.S. Pat. No. 6,113,637 by Gill et al. This artificial spinal disc incorporates a ball and trough type articulation with a substantially flat portion. Both the Yuichiro and Gill et al. patents describe devices which rely on point contact, a potential source of excessive wear debris.

The disclosed invention, in the form of first and second articulating components to be positioned between adjacent vertebral bodies, provides a more controlled rotation or in the alternative a controlled rotation with translation in one plane only, incorporating either surface to surface, or surface to line contact. As a result any translation away from the center in the one plane will produce device and joint distraction thereby providing a self-governing resistance to limit excessive translation.

The several disclosed embodiments of the invention provide two additional advantages over the more common artificial disc devices. The first is that the components or the majority of the parts of a composite components may be made of radio translucent or partially radio translucent material depending on the desired outcome. This greatly increases the ability for the device, surrounding tissue and bone to be evaluated using standard medical imaging techniques. The second advantage is that the parts of each composite component (for each articulating side) may be manufactured as one integrally formed unit. This reduces interconnected parts micro-motion and wear while increasing the system's ease of use.

SUMMARY OF THE INVENTION

In a broad sense a motion restoring prosthesis adapted to be placed between the ends of two bones adjoining a mammalian appendage or spinal joint, in accordance with the present invention, includes two components with each component defining an outer surface for attachment to a respective bone end and an articulating surface for engaging the articulating surface of the other component. At least one of the components has an inner and outer section. The inner section, defining the articulating surface, is made of a primary relatively hard/stiff material such as ceramic, cobalt chromium, or other hard, stiff bio-compatible material for inhibiting the wear between the articulating surfaces. The outer section is made of a secondary material (sometimes hereinafter referred to as the "bone buttressing material") that is softer and less stiff than the primary material (sometimes referred to as the "articulating material"). Preferably the secondary material is formed of a biocompatible polymer having a hardness/stiffness characteristic closer to that of the bone to be buttressed. Polyetheretherketone ("PEEK") or carbon fiber reinforced PEEK ("CFRPEEK") are clear choices. These polymers reduce stress shielding by more evenly distributing the forces or load from the articulating surfaces to the respective bone interface end thereby enhance the life of the prosthesis.

Preferably the flexural moduli of the primary and secondary materials are, respectfully, within the range of about $80\pm$ and about 60 or less on the Giga Pascal Scale (GPa), which scale provides a measure of elasticity versus pressure. Most preferably the secondary material has a GPa range of about 4 to 30 or about 12-25 while cortical bone has a GPa of about $17\pm5$-8.

Optionally, the bone buttressing surface of each of the outer sections are roughened and/or made uneven to enhance the attachment of bone thereto. Further, it is desirable for the bone buttressing surface to have a very thin coating or layer of a bone-on growth attachment friendly material, such as titanium, calcium phosphate or hydroxyapatite thereon, which does not materially increase the stiffness of the bone buttressing surface of the secondary material to detract from the stress shielding characteristic thereof, while enhancing the attachment of the bone thereto. Preferably the thin coating of such material is within the range of about 0.5 to 15.0 or more microns and most preferably within the range of about 0.50 to 3.0 microns.

In a narrower sense, and particularly for creating artificial spinal joints, both components are formed with inner and outer sections. The inner sections are formed of the primary material and preferably define a ball and socket type articulating surface as described in the '744 application. The outer sections are formed of the softer secondary material which define the bone buttressing surfaces for attachment to the respective bone faces of the separated vertebral bodies.

Again, it is preferable that the softer outer sections partially encapsulate the inner sections, e.g., by an injection molding process, to substantially prevent any motion including macromotion between the inner and outer sections.

With respect to item (b) an artificial intervertebral disc or spacer, for accommodating fusion, is preferably formed of a material such as PEEK or CRFPEEK having a flexure modulus comparable to that of cortical bone. The spacer is provided with a roughened and/or uneven surface and subsequently provided with a very thin coating of a material such as Ti which enhances bone-on growth without adversely affecting the bone friendly surface characteristic of the PEEK or CFRPEEK as discussed above.

The present invention is directed to several embodiments of a motion restoring intervertebral device. The device is designed to partly or completely replace a spinal disc. The device comprises a superior and an inferior end plate (i.e., first and second components) which will buttress against and maintain separation between adjacent vertebral bodies. Each of the components has a vertebral body ("vertebral") engaging surface and an articulating surface. The vertebral engaging surfaces may be generally flat, tapered, or slightly convex to accommodate the vertebral body anatomy and centralized compaction. Such vertebral engaging surfaces may include any number of keels, pegs, recesses, protrusions or other means of mechanically fixating the components to the vertebral bodies. The vertebral engaging surfaces may be further enhanced with a porous coating, grit finishing, fusion deposition coating, biological coating or chemical coating designed to enhance long term bone fixation to the inserted device.

In one embodiment the articulating surface of a first component is in the form of a circular domed convex projection, e.g., a semispherical center section preferably merging with an outer toroidal protrusion in the form of an encircling or partially encircling generally semi-cylindrical concave end section terminating in an outer lip or rim. The articulating surface of the second component mates with the articulation surface of the first component to allow the two components to rotate and tilt relative to each other. The second component's articulating (or mating) surface is in the form of a circular shaped concave recess, e.g., a semispherical concave center section which is preferably joined to an encircling or partially encircling end section terminating in an outer lip.

In a second embodiment the articulating surface of the second component is formed with a swept radial convex recess forming a two dimensional cross section, similar to an ellipse, in which the radial diameter mates with the circular domed convex projection of the first component to produce a generally conforming articulation in the plane of the radial convex recess of the second component and non-conforming articulation out of this plane.

One option is to form each of the components, other than a surface alteration to the vertebral engaging surfaces for composite components, entirely from a low wear material.

Another option is to form the vertebral engaging surfaces of a secondary material which is softer than the material forming the articulating surfaces to dampen the stress transfer from a hard low wear articulation material to the vertebral body.

Another option is to configure the secondary material to provide a mechanical locking feature.

Additionally, components or parts thereof may be made of a radio translucent or partially radio translucent material as to allow for unobscured imaging of the surrounding bone and tissue using X-Ray, MRI, or CAT Scan techniques.

In addition, the components or the articulation surfaces may be formed by injection molding to reduce or eliminate the potential of micro-motion and wear while allowing for precision fabrication.

The invention may best be understood in reference to the following description taken in conjunction with the appended drawings where like components and parts thereof are given the same numerals in the several figures.

BRIEF DESCRIPTION OF THE DRAWINGS

FIGS. 4A, 4B, and 4C are assembled and cross-sectional views of the device of FIG. 3 showing the sept radius feature of the articulations;

FIG. 5 is a side elevational view of an intervertebral device in which the components forming the articulation and vertebral engaging surfaces are composed entirely of a single low wear material;

FIGS. 6A and 6B are cross-sectional views of an intervertebral device in which the opposing articulation surfaces are mated with secondary material forming the vertebral engaging surfaces;

DETAILED DESCRIPTION OF THE INVENTION

Figure 1:
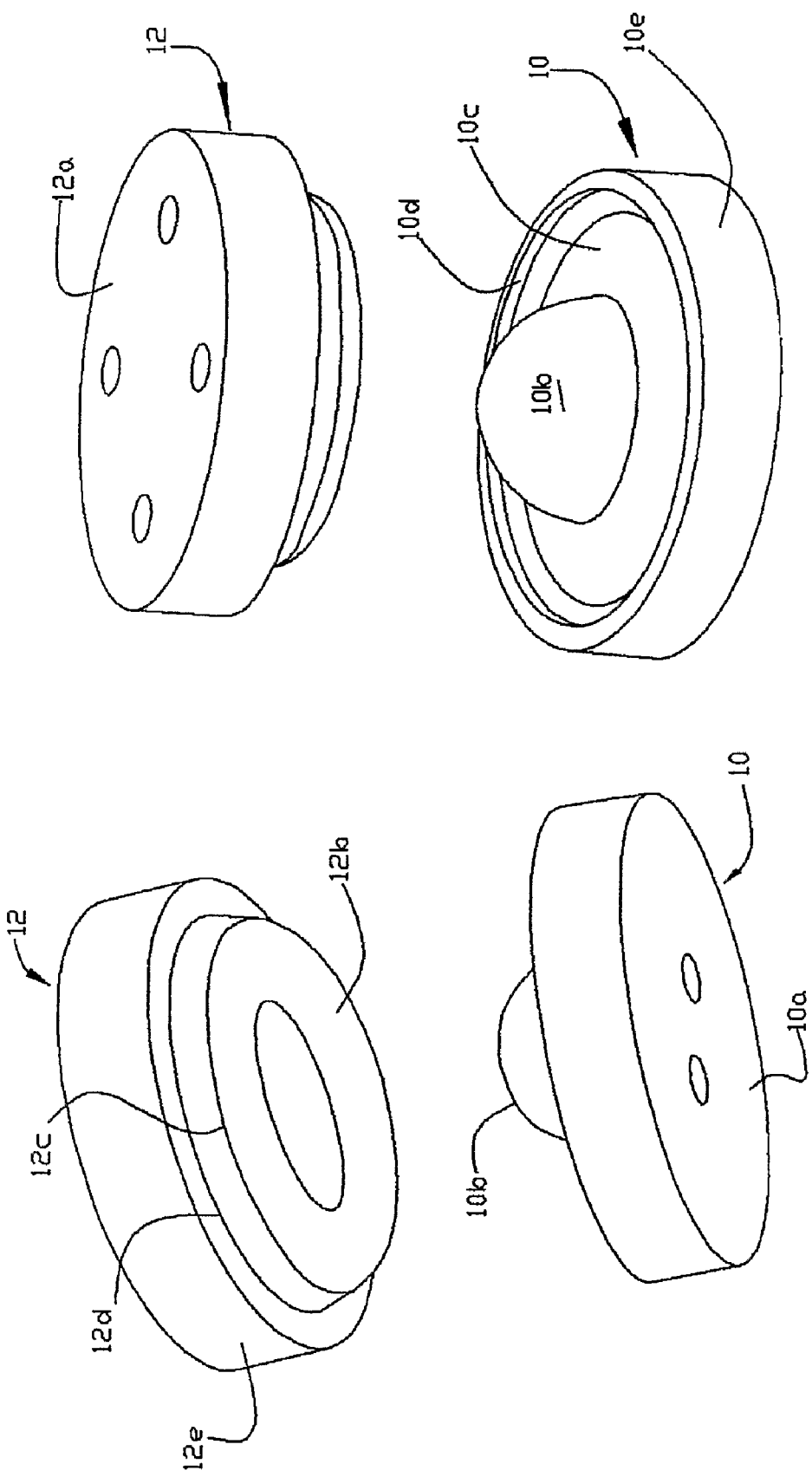
FIG. 1 contains two isometric or perspective views of an unassembled intervertebral device having circular domed and toroid shaped articulation surfaces.
Figure 2:
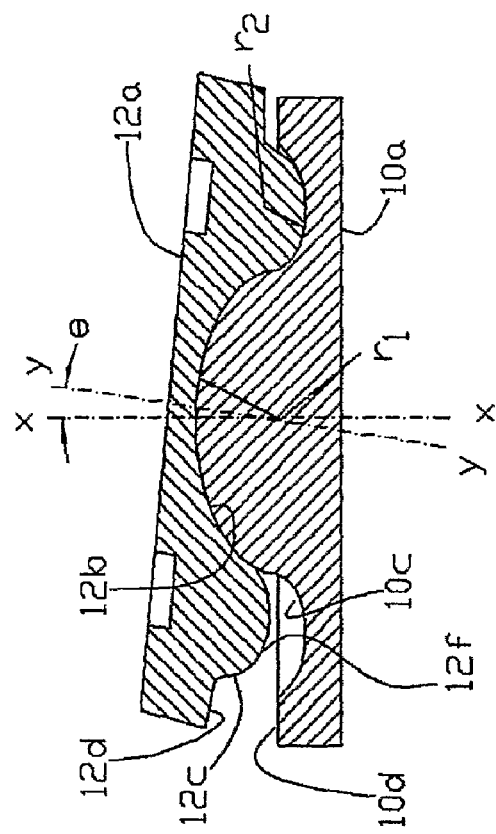
FIG. 2 contains a perspective and cross-sectional view of the device of FIG. 1.
Figure 2:
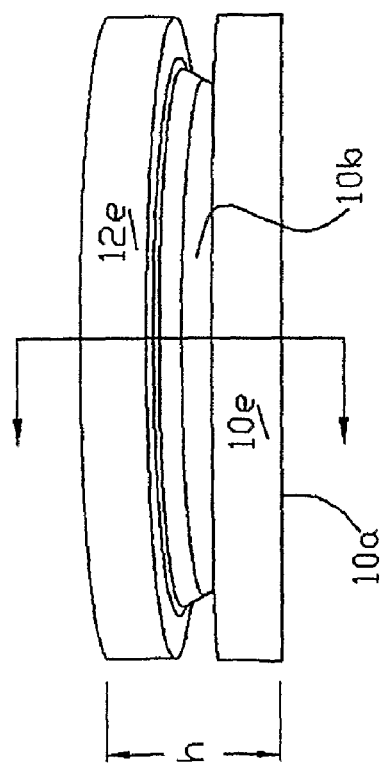

Referring now to FIGS. 1 and 2, a motion restoring intervertebral device comprises first and second components 10 and 12 with component 10 having a vertebral engaging surface 10a for buttressing against a vertebral body and an articulating surface in the form of a dome, e.g., generally semispherical convex center section 10b joined to or merged with an encircling revolved concave recess, e.g., a generally semi-cylindrical concave end section 10c which terminates in an outer lip or rim 10d. Component 12 has a vertebral engaging surface 12a for buttressing against an opposing vertebral body and a mating/articulating surface in the form of a generally semispherical concave center section 12b joined to an encircling end section 12c, having a generally semi-cylindrical convex cross-section, terminating in an outer lip or rim 12d. A peripheral wall 10e and 12e extends between the two surfaces of components 10 and 12, respectively. The radius $r_2$ of the center sections (10b, 12b) is within the range of about 0.1 to 1.0 inches depending upon whether the components are to be used in the thoracic, lumbar, or cervical region and the patient's anatomy. The radius r.sub.2 of the end sections (10c, 12c) is within the range of about 0.05 to 0.3 inches depending upon the above factors. The overall height h of the two mating components should be within the range of about 0.19-0.315 inches and 0.315 to 0.8 inches for use in the thoracic and lumbar regions, respectively, dependent upon the patient's anatomy.

The circular domed articulation 10b, while shown as completely encircled by the revolved concave recess end section, may be only partially encircled by such an end section. First and second outer rims 10d and 12d extend generally horizontally outwardly from the convex and concave center sections of the first and second components, respectfully. These rims provide additional stability to components. The engagement of the rims limits the tilting action between the articulating surfaces, i.e., to restrict the angular movement of the second component with respect to the first component to an angle θ relative to a vertical axis perpendicular to the plane of the first component as is illustrated by the axii xx and yy in FIG. 2. Additional device articulation of the components onto the apex 12f of the toroid 12c and the convex recess 10c will induce device and joint distraction, thus producing a self governing resistance to excessive rotation. The domed and toroid shaped articulations may be conforming to restrict translation or nonconforming to anticipate joint translation.

Figure 3:
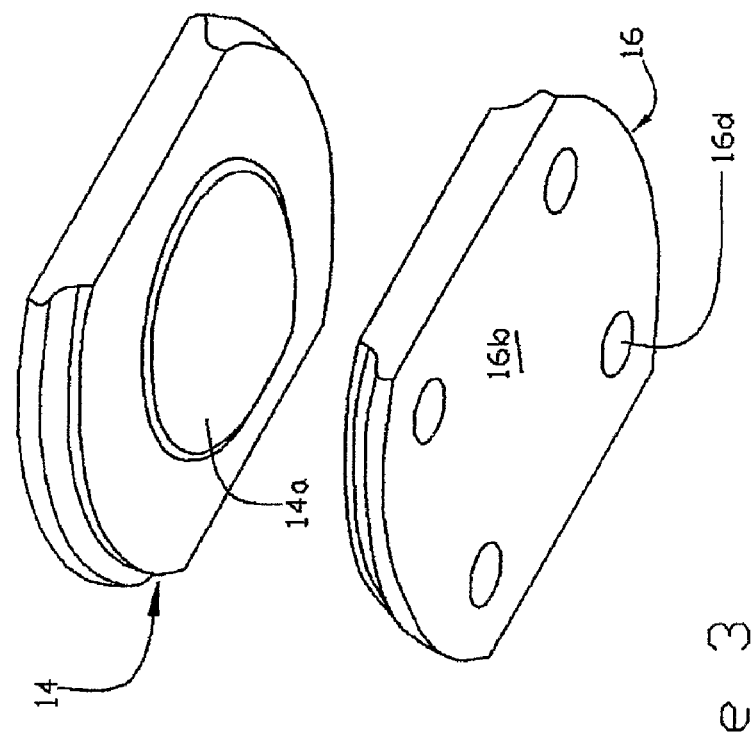
FIG. 3 contains two isometric or perspective views of an intervertebral device with a circular domed and swept radius articulations.
Figure 3:
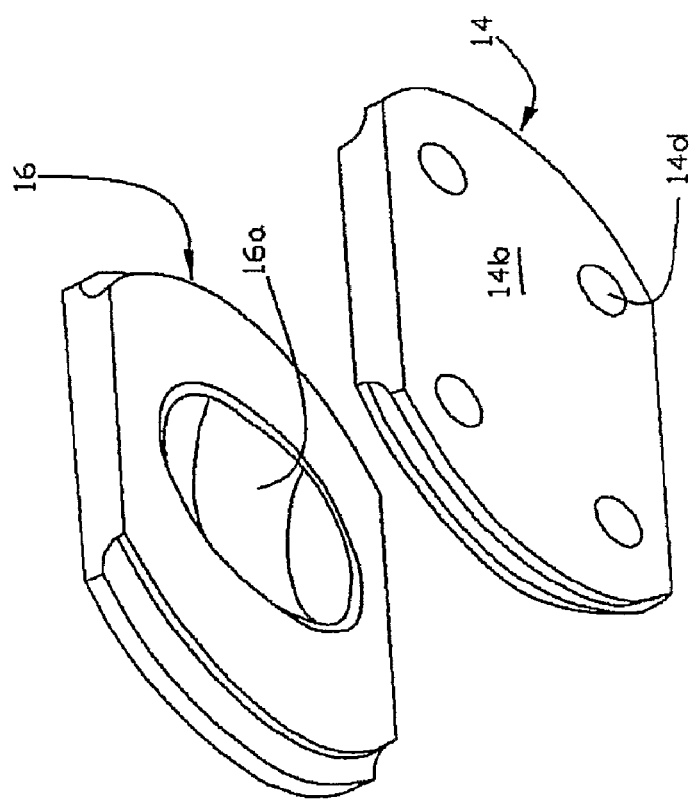

FIGS. 3 and 4 show a second embodiment wherein a first component 14 includes a dome or partial spherical articulating surface 14 a which articulates within a concave swept radius partially spherical articulating surface 16a in component 16. The articulating surface 16a has a first radius $r_3$, preferably in the medial lateral or frontal plane, as illustrated in FIG. 4B, to be generally conforming to the radius of the circular dome 14a and a sweeping radius $r_4$ in medial section 16c, preferably in the anterior posterior or sagittal plane, to be generally non-conforming and larger than the radius $r_3$ of the circular dome. This allows for generally line to line articulation contact with controlled rotation in the said frontal plane and controlled rotation with translation in the sagittal plane. Any translation away from the center of the sweeping radius $r_4$ will produce device and joint distraction, thus a self governing resistance to translation. The vertebral engaging surfaces 14b and 16b are illustrated with option depressions 14d and 16d for receiving anti-migration pins to be described in connection with FIGS. 5 and 6.

FIG. 5 is an example of the components with their articulation (14'a, 16'a) and vertebral/buttress surfaces made of a single low wear material in which 14' and 16' designate the components with the dome and concave articulating surfaces, respectively. The vertebral engaging surfaces are illustrated as including protrusions 15 for fixing the components to the respective vertebral bodies.

FIGS. 6A and 6B show exemplar devices in which the articulation surfaces, formed in a primary material 22, are partially enclosed by a secondary material 20. The secondary material may be secured to the primary material with a chemical or mechanical lock. For example, outwardly extending protrusions 22a in the primary material 22 may be overlapped by an inwardly extending protrusions 20a in the primary material. The secondary material will provide benefits that a hard articulating surface may not provide. For example, if softer than the articulating surface, the secondary material will provide a stress dampening between the hard articulation surface and the bone. The primary material may have a flexural modulus on the Giga Pascal Scale (GPa) of 70 or greater and the secondary material preferably has a GPa flexural modulus of 60 or less and preferably less than 30. See the more detailed description of such properties in the companion PCT application based on the '744 application and filed on even date herewith. The contents of such PCT application is incorporated herein by reference. The secondary material will also provide a means to encapsulate and hold additional mechanical vertebral end plate stabilization features of such as titanium pins or pegs 24 resting in recess 26 of the articulating (primary) material 22. The pegs may be configured into other mechanical locking features such as keels, crosses, circles etc. The secondary material will also provide a different medium for attachment of surface enhancements.

Figure 7B:
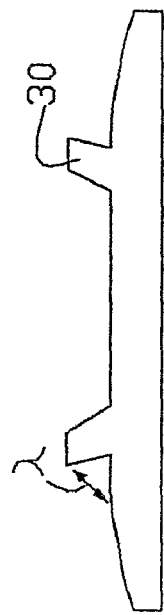
FIGS. 7A and 7B are perspective and cross-sectional views of keels disposed in the vertebral engaging surfaces and examples of mechanical locking features for securing two materials of different hardness values together.
Figure 8:
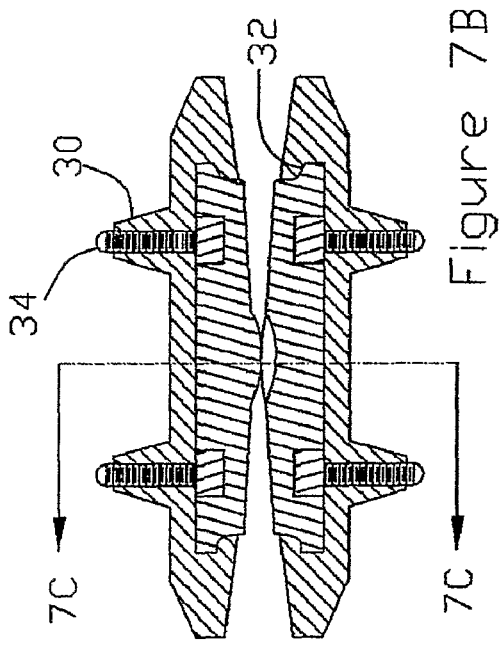
FIG. 8 is a side elevational view of an alternate keel design for the vertebral engaging surfaces.
Figure 7A:
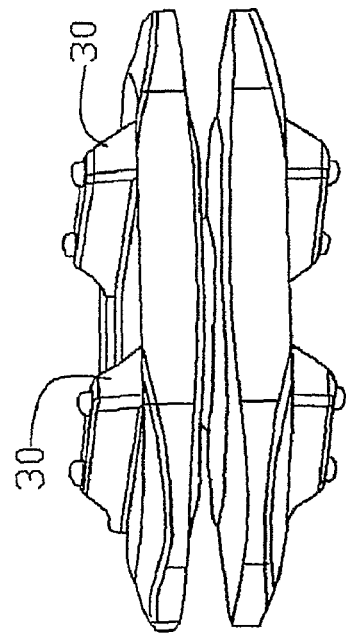
Figure 7C:
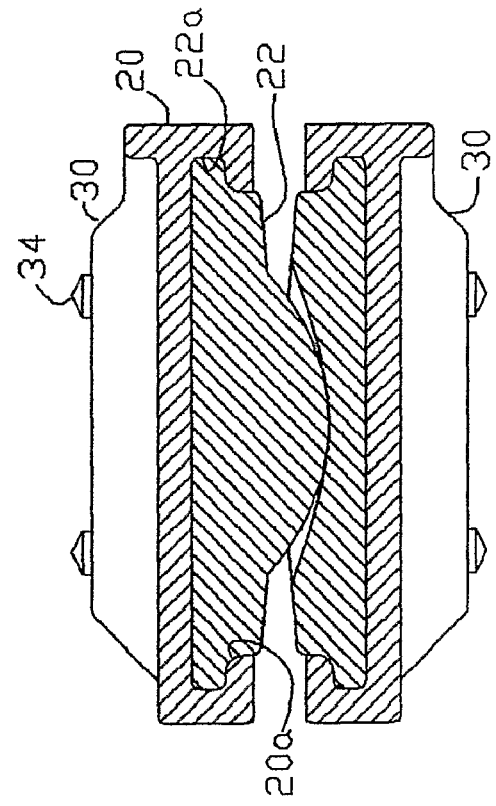
FIG. 7C is a cross-sectional view of the device of FIGS. 7A and 7B taken along lines 7C-7C of FIG. 7B.

FIGS. 7A and 7B illustrate one such alternative end plate configuration with keels 30 and an anterior lip 32. Pegs 34 are an optional embodiment embedded within the keels to provide for fabrication simplification, imaging markers, and/or added strength. The pegs may exist as shown or as a rail located on the outermost edge of the keel for device insertation strength and mechanical fixation. The keels 30 may be generally perpendicular to the prosthesis or any edge angle towards the end plate as show in FIG. 8. A keel angled towards the end plate, i.e., at angle λ less than 90 degrees, will produce a mechanical lock to the bone end plate when inserted.

The preferred means for fabrication is injection molding a polymer around the articulating surfaces to provide for a stable interface.

By forming the articulating surfaces from a ceramic material 22, the encapsulation material 20 from a polymer such as PEEK or carbon reinforced PEEK, and using titanium fixation pins 24 or 34, the device will be partially to fully radio translucent, extremely wear resistant, and limit stress shielding to the vertebral end plates.

The secondary material should have a flexural modulus on the GPa scale of about 60 or less and preferably within the range of 4 to 30 and most preferably about 17±5-8 which is the flexural modulus spectrum of cortical bone. The primary material may be made of a bio-compatible ceramic, e.g., alumina ceramic, which has a GPa flexural modulus of about 158±10% while another suitable primary materials is cobalt chromium alloy (including some molybdenum) which has GPa flexural modulus of about 80.

PEEK is an excellent implantable bio-compatible material suitable for use as the secondary material with a GPa flexural modulus of about 4 and when reinforced with 20% carbon fiber has a GPa of about 18. The carbon fiber content may be adjusted from 0 to about 80%, but we have found that a mixture of about 30 to 35% of carbon fiber by weight provides a preferred bone-to-implant surface while providing sufficient support for the molded insert of articulating (primary) material and it has a stiffness slightly higher than the average (i.e., about 17 GPa) for cortical bone, but less than 30 GPa, i.e, about 21-24, while being imaging friendly, i.e., translucent to the conventional imaging processes.

The outer surfaces of the bone-to-implant surface can be formed of the secondary material and coated with a very thin layer of a material which promotes the affixation of bone to the bone buttressing surfaces while essentially maintaining the ability of such surfaces to accommodate surface irregularities of the bone face and provide stress softening. We have found that a very thin coating of Ti, calcium phosphate or hydroxyapatite serves this purpose. Such coating or layer can be applied by a conventional vacuum/electronic ionic fusion processes. As pointed out earlier, such a coating should have a thickness within the range of about 0.5 to 15.0 microns and most preferably between about 0.5 to 3.0 microns. It should be noted that such a coating on a prosthesis component made of the described secondary material forming a bone buttressing surface may be useful independently of the material forming the articulating surface.

The secondary material of the bone-to-implant surface can be roughened by an apparent blast media or tumbled in an abrasive media to create a micro surface roughening.

The secondary material is then coated with a thin micron layer (i.e., 0.5 to 3-10 microns) of a material e.g., Ti, calcium phosphate or hydroxyaptite, which will promote bone-on growth without materially modifying the stress transfer characteristic between the soft material and the bone.

There has been described a novel prosthesis for restoring motion in an appendage or spinal joint which employs a relatively hard-stiff material to form the articulating surfaces while employing a softer less stiff material to form one or both bone buttressing surfaces to inhibit wear at the articulating surfaces while reducing stress shielding at the prosthesis bone interface(s). Preferably the softer material is provided with a thin micron coating of a material which promotes bone attachment without adversely affecting the reduction in stress shield.

The polymer surface may be enhanced for bone on-growth or mechanical interlocking by first roughening the vertebral engaging surfaces and coating them with a thin layer of titanium or a titanium blend. The preferred method of roughening is with a resorbable blast media or by roughening the opposing surfaces of the injection mold tooling. The advantage of these methods is that no trace elements remain from an alternative roughening method such as grit blasting. The preferred method of titanium coating is ionic fusion deposition. This method does not apply excessive heat to the surface, such as the case with titanium plasma spray, which may damage the polymer. A second advantage of this method is that it is applied in a very thin layer, thus allowing the rest of the device to be larger and stronger. This method for a surface enhancement may be applied to any device requiring bone on-growth and/or mechanical interlocking.

There has thus been described a novel motion restoring intervertebral device providing controlled and/or translation motion between the two components forming the device. The use of radio translucent materials for the components or parts thereof allow for unobscured or only partially obscured imaging of the surrounding bone and tissue using conventional imaging machines. Various modifications an perhaps improvements to the disclosed embodiments will undoubtedly occur to those skilled in the art without involving any departure from the spirit and scope of the invention as defined by the appended claims.

The invention claimed is:

1. An intervertebral device designed to partially or completely replace a natural spinal disc, comprising:
    a first component having a first vertebrae engaging surface configured to buttress against a first vertebral body and a lower articulating surface; and
    a second component having an upper articulating surface, with a flexural modulus on a GPa scale of about 70 or greater, and configured to complement the lower articulating surface of the first component to permit relative movement and a second vertebral engaging surface configured to buttress against a second vertebral body, the first component and second component are of a shape to be respectively positioned between the first vertebral body and the second vertebral when replacing a natural spinal disc,
    wherein the first vertebral engaging surface and second vertebral engaging surface are formed of a polymer having a roughened surface configuration to enhance a bone forming growth and a mechanical interlocking with an adjacent vertebral body surface, the roughened surface is coated with a solid thin micron range layer of titanium as a bone growth enhancing material to maintain and replicate, on the solid titanium coating outer surface, the underlying roughened surface characteristic to enhance a bone forming growth between the respective first and second vertebral engaging surfaces and the respective first and second vertebral bodies of a spine when implemented in a user's spine, wherein the first and second vertebral engaging surfaces are polyetheretherketone and coated with the solid thin titanium layer having a characteristic of not adversely affecting bone stress force transfer characteristics from the vertebral first and second bodies through the solid thin titanium layer to the respective first and second components of polyetheretherketone engaging surfaces, wherein the first and second vertebral engaging surfaces have a flexural modulus on a GPa scale within the range of about 4-25.

2. The intervertebral device of claim 1 wherein the first and second vertebral engaging surfaces include one or more integral keels of polyetheretherketone extending upward from the respective first and second vertebral engaging surfaces.

3. The intervertebral device of claim 2 wherein a pair of integral keels are provided on each of the first and second vertebral engaging surfaces and are angled towards an adjacent perimeter of the respective component to provide a mechanical lock when engaged with an adjacent vertebral surface.

4. The intervertebral device of claim 1 wherein the lower articulating surface and the upper articulating surface have complementary curvilinear surfaces to enable rotational movement.

5. The motion restoring prosthesis of claim 1 wherein the solid thin titanium layer has a thickness within a range of 0.5 to 15 microns.

6. The intervertebral device of claim 1 wherein the prosthesis is an artificial spinal disc with the bone facing surfaces being generally planar to buttress respective vertebral bodies.

7. A motion restoring prosthesis to be interposed between the ends of mammalian bones adjoining a natural appendage or spinal joint to provide articulation therebetween comprising:
    two components, each component defining an outer surface for attachment to a respect bone end and an articulating surface for engaging the articulating surface of the other component;
    at least one of the components having an inner and outer section, the inner section defining the articulating surface and being formed of a primary, relatively hard, stiff material having a first flexural modulus, the outer section defining a bone facing surface to be attached to one of the bone ends and formed of a secondary softer material having a second flexural modulus, the first flexural modulus being greater than the second flexural modulus, the outer section functioning as a stress shielding softening material to more evenly distribute forces transmitted through the articulating surfaces and the associated bone end, wherein the bone facing surface of said at least one component has been roughened and/or made uneven to enhance an attachment of adjacent bone and covered with a thin coating containing Ti within a range of thickness to enable bone-on growth with the roughened and/or uneven bone facing surface while maintaining an appropriate distribution of forces through the thin coating containing Ti to permit the stress shielding characteristic of the coated secondary softer material to be operative, wherein the first flexural modulus is about 70 or greater on the GPa scale and the second flexural modulus is about 60 or less on the GPa scale.

8. The motion restoring prosthesis of claim 7 wherein the secondary material is PEEK with or without the presence of carbon fiber reinforcement.

9. A motion restoring prosthesis to be interposed between the ends of mammalian bones adjoining a natural appendage or spinal joint to provide articulation therebetween comprising:
    two components, each component defining an outer surface for attachment to a respect bone end and an articulating surface for engaging the articulating surface of the other component;
    at least one of the components having an inner and outer section, the inner section defining the articulating surface and being formed of a primary, relatively hard, stiff material having a first flexural modulus, the outer section defining a bone facing surface to be attached to one of the bone ends and formed of a secondary softer material having a second flexural modulus, the first flexural modulus being greater than the second flexural modulus, the outer section functioning as a stress shielding softening material to more evenly distribute forces transmitted through the articulating surfaces and the associated bone end, wherein the bone facing surface of said at least one component has been roughened and/or made uneven to enhance an attachment of adjacent bone and covered with a thin coating containing Ti within a range of thickness to enable bone-on growth with the roughened and/or uneven bone facing surface while maintaining an appropriate distribution of forces through the thin coating containing Ti to permit the stress shielding characteristic of the coated secondary softer material to be operative, wherein the secondary material has a flexural modulus on the GPa scale within the range of about 4-25.

10. The motion restoring prosthesis of claim 9 wherein the secondary material is one of PEEK without the presence of carbon fiber and PEEK with the presence of carbon fiber.

11. The motion restoring prosthesis of claim 9 wherein the prosthesis is an artificial spinal disc with the bone facing surfaces being generally planar to buttress respective vertebral bodies.

12. The motion restoring prosthesis of claim 9 wherein the solid thin titanium layer has a thickness within a range of 0.5 to 15 microns.

* * * * *